United States Patent [19]

Szirt nee Kislelly et al.

[11] Patent Number: 5,597,822
[45] Date of Patent: Jan. 28, 1997

[54] PHARMACEUTICAL COMPOSITIONS FOR THE PREVENTION AND/OR TREATMENT A GASTROINTESTINAL DISEASES

[75] Inventors: Eniko Szirt nee Kislelly; Zoltan Budai; Tibor Mezei; Gabor Blasko; Klara Kazo nee Daroczi; Andras Egyed; Gabor Gigler; Marton Fekete; Klara Reiter nee Esses; Gyula Simig; Katalin Szemeredi, all of Budapest, Hungary

[73] Assignee: Egis Pharmaceutical, Budapest, Hungary

[21] Appl. No.: 443,487

[22] Filed: May 18, 1995

Related U.S. Application Data

[63] Continuation-in-part of Ser. No. 277,072, Jul. 19, 1994, abandoned.

[30] Foreign Application Priority Data

Jul. 20, 1993 [HU] Hungary .................... 20579/93

[51] Int. Cl.[6] .................. A61K 31/50; A61K 31/495; A61K 31/505; A61K 31/15
[52] U.S. Cl. .................. 514/247; 514/255; 514/256; 514/640
[58] Field of Search .................... 514/247, 255, 514/256, 640

[56] References Cited

U.S. PATENT DOCUMENTS 5,130,487  7/1992  Budai et al. ..................... 564/256
5,234,934  8/1993  Budai et al. ..................... 514/331

*Primary Examiner*—Kimberly Jordan
*Attorney, Agent, or Firm*—Beveridge, DeGrandi, Weilacher & Young, LLP

[57] ABSTRACT

The invention refers to pharmaceutical compositions for the prevention and/or treatment of gastrointestinal diseases connected with infections caused by *Helicobacter pylori* and a method for the treatment of such diseases.

The pharmaceutical composition of the invention comprises as active ingredient a cyclic ketone derivative of the formula I

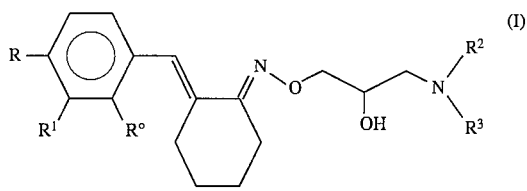

wherein and $R^1$ mean independently hydrogen or halo;

$R^0$ stands for hydrogen or a $C_{1-4}$ alkoxy group;

$R^2$ and $R^3$ independently represent hydrogen; a straight or branched chain $C_{1-8}$ alkyl optionally substituted by a dimethylamino group; a $C_{2-6}$ alkenyl or a $C_{3-7}$ cycloalkyl group; or $R^2$ and $R^3$ together with the adjacent nitrogen atom form a 6-membered heterocyclic group containing an additional nitrogen atom that may bear a phenyl group optionally substituted by a $C_{1-4}$ alkoxy group;

or its stereoisomer or optical isomer or a possible mixture thereof, or a pharmaceutically acceptable acid addition salt or quaternary ammonium salt thereof in admixture with carrier(s) commonly used in pharmaceutical compositions.

1 Claim, No Drawings

PHARMACEUTICAL COMPOSITIONS FOR THE PREVENTION AND/OR TREATMENT A GASTROINTESTINAL DISEASES

REFERENCE TO A RELATED APPLICATION

This is a continuation-in-part of our application Ser. No. 08/277,072 filed 19 Jul. 1994, now abandoned, which is relied on and incorporated herein by reference in its entirety.

The invention refers to pharmaceutical compositions for the prevention and/or treatment of gastrointestinal diseases and a method for the treatment of such diseases.

It is known that ketone derivatives of the formula

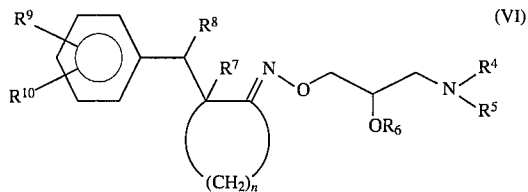

wherein $R^9$ and $R^{10}$ independently stand for hydrogen, halo, a lower alkoxy group or $R^9$ and $R^{10}$ together form a methylenedioxy group;

$R^7$ and $R^8$ both represent hydrogen or $R^7$ and $R^8$ together form a chemical bond;

$R^4$ and $R^5$ mean, independently from each other, hydrogen, a straight or branched chain, saturated or unsaturated $C_{1-12}$ alkyl group being optionally substituted by a dialkylaminoalkyl, dimethoxyphenyl or phenyl group; or a $C_{3-7}$ cycloalkyl group;,or $R^4$ and $R^5$, together with the adjacent nitrogen atom, form a 4–7 membered heterocyclic group comprising optionally an additional oxygen, sulfur or nitrogen atom and the additional nitrogen atom optionally may bear a phenyl, benzyl or $C_{1-3}$ alkyl group, and optionally the latter substituents may be substituted by a hydroxyl group or one or two methoxy groups(s), halogen atom(s) or trifluoromethyl group(s); or $R^4$ and $R^5$, together with the adjacent nitrogen atom, form a piperidine ring optionally containing a double bond and optionally substituted by a phenyl or benzyl group;

$R^6$ stands for a hydrogen atom or a benzoyl group; and n is 3, 4, 5 or 6, possess antianginal and/or antiarrhythmic, gastric acid secretion inhibiting, local anaesthetic, tranquillo-sedative, antiinflammatory, analgetic and, in some cases, calcium antagonist effects (GB-P 2,235,198, U.S. Pat. Nos. 5,130, 487 and 5,234,934).

Recently, gastric and duodenal ulcers are among the most widespread diseases that are accompanied by a continuously increasing number of oesophagitis reflux cases. It is more and more believed by clinical practitioners that the most adequate method for the treatment of peptic ulcer consists in killing the *Helicobacter pylori* bacteria being present in the organism of the patient. The antiulcer use of ranitidine /8-(5-dimethylaminomethyl-2-furyl)-3-nitromethylene-7-thia-2,4-diazaoctane/ and cimetidine /2-cyano-1-methyl-3-[2-[[(5-methyl-4-imidazolyl)-methyl]thio]ethyl]guanidine/ having an otherwise favourable histamine $H_2$ receptor antagonist effect was highly diminished by the discovery that the killing of *Helicobacter pylori* prevents the relapse of ulcer. As a consequence, the use of omeprazole 5-methoxy-2-[[(4-methoxy-3,5-dimethyl-2-pyridyl)methyl]sulfinyl]] benzimidazole/ inhibiting the $H^+/K^+$-ATP-ase enzyme becomes more and more widespread (this mechanism of action is quite novel compared to those known in the art). Its spreading is significantly promoted by the safety of its therapeutical use and the low number of side effects.

Compounds inhibiting the proton pump i.e. being inhibitors of $H^+/K^+$-ATP-ase are not only preferred and more rapidly acting compounds than the $H_2$ antagonists, but, in comparison to $H_2$ antagonists, they are effective also in the treatment of aesophagitis reflux, which is becoming more and more widespread. A common drawback of the antiulcer drugs possessing various mechanisms is that they do not represent an effective therapeutical method against *Helicobacter pylori* bacteria. At present, omeprazole is combined with amoxycillin /(2S,5R,6R)-6-[(R)-(–)-2-amino-2-(p-hydroxyphenyl)acetamido]-3,3-dimethyl-7-oxo-4-thia-1-azabicyclo/3.2.0/heptane-2-carboxylic acid/ having antibacterial activity to obtain better therapeutical result. Previously, the combination of colloidal bismuth and metronidazole /2-methyl-5-nitroimidazole-1-ethanol/ with amoxycillin had been used, but metronidazole caused a great problem since, in addition to its rather unfavourable side effects, bacteria became increasingly resistant to it.

As an inhibitor of the proton pump, omeprazole plays some role in the prevention of ulcer development caused by nonsteroidal antiinflammatory drugs. At present, cetraxate /trans-3-[4-[4-(aminomethyl)cyclohexylcarbonyloxy]phenyl]-propionic acid/ and sucralfate /beta-D-fructofuranosyl alpha-D-glucopyranoside hydrogen sulfate basic aluminium salt/ are the most frequently used ulcer preventing and cytoprotective agents.

Thus, there is a demand on a pharmaceutical composition simultaneously exerting:

a) a rapid ulcer healing effect;

b) a prophylactic effect against ulcer formation induced by nonsteroidal antiinflammatory drugs; and c) an effect of completely killing the *Helicobacter pylori* bacteria without the risk of intolerable side effects.

The aim of the invention is to provide pharmaceutical compositions having the above effects.

It was found that the compounds of the formula I

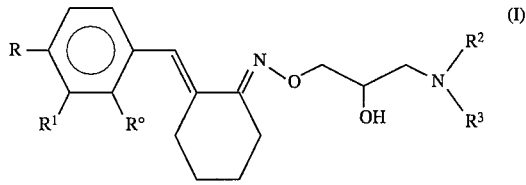

falling within the scope of formula VI, where in the formula I

R and $R^1$ mean independently hydrogen or halo;

$R^0$ stands for hydrogen or a $C_{1-4}$ alkoxy group;

$R^2$ and $R^3$ independently represent hydrogen; a straight or branched chain $C_{1-8}$ alkyl optionally substituted by a dimethylamino group; a $C_{2-6}$ alkenyl or a $C_{3-7}$ cycloalkyl group; or $R^2$ and $R^3$ together with the adjacent nitrogen atom form a 6-membered heterocyclic group containing an additional nitrogen atom that may bear a phenyl group optionally substituted by a $C_{1-4}$ alkoxy group;

as well as their stereoisomers or optical isomers and possible mixtures thereof, furthermore the pharmaceutically acceptable acid addition salts or quaternary ammonium salts of the above compounds possess valuable gastroprotective and anti-microbial activity, said gastroprotective activity being independent of the inhibition of the gastric acid secretion. Consequently, the cyclic ketone derivatives of the formula I can be utilized as active agents of pharmaceutical compositions useful for the prevention and/or treatment of gastrointestinal diseases.

Thus, the invention relates to a cytoprotective pharmaceutical composition comprising as active ingredient a cyclic ketone derivative of the formula I or its stereoisomer or optical isomer or a mixture thereof, or a pharmaceutically acceptable acid addition salt or quaternary ammonium salt of these compounds.

In the description "cytoprotection" is defined as the ability of certain compounds to protect the organs of the digestive system against deteriorative effects. In case of the gastrointestinal system, "cytoprotection" is also called "gastroprotection". Therefore, in the description the expressions "cytoprotection", "cytoprotective" and "gastroprotection", "gastroprotective", respectively, are used as synonyms Furthermore, the invention refers to a method for the treatment of gastrointestinal diseases connected with infections caused by *Helicobacter pylori*.

In formula I, halo means fluoro, chloro, bromo or iodo, preferably chloro or bromo.

A $C_{1-4}$ alkoxy group can be a methoxy, ethoxy, n-propoxy, isopropoxy, n-butoxy, isobutoxy, sec.-butoxy or tert.-butoxy group.

A straight or branched chain $C_{1-8}$ alkyl group is for example a methyl, ethyl, n-propyl, isopropyl, n-butyl, pentyl, hexyl, heptyl or octyl group.

A $C_{2-6}$ alkenyl group is for example a propenyl, butenyl, pentenyl or hexenyl group.

A $C_{3-7}$ cycloalkyl group is a cyclopropyl, cyclobutyl, cyclopentyl, cyclohexyl or cycloheptyl group.

The compounds of the formula I comprise chiral carbon atoms as well as double bonds, thus, stereoisomers and optical isomers may exist. The pharmaceutical compositions of the invention may comprise such stereoisomers or optical isomers or possible mixtures thereof.

Preferred pharmaceutical compositions of the invention comprise cyclic ketone derivatives of the formula I, wherein R, $R^1$ and $R^0$ are as defined above, $R^2$ and $R^3$ independently represent hydrogen; a straight or branched chain $C_{1-6}$ alkyl optionally substituted by a dimethylamino group; a $C_{2-4}$ alkenyl or a cyclohexyl group; or $R^2$ and $R^3$ together with the adjacent nitrogen atom and with a further nitrogen atom form a piperazinyl group substituted by a methoxyphenyl group;

as well as their stereoisomers or optical isomers and possible mixtures thereof, furthermore the pharmaceutically acceptable acid addition salts or quaternary ammonium salts of the above compounds.

Representatives of the compounds of the formula I which show particularly preferred properties in the pharmaceutical compositions of the invention are as follows:

Compound A: (R,S)-2-(E)-(3,4-dichlorophenylmethylene)-1-(E)-[(3-butylamino-2-hydroxypropoxy)imino]cyclohexane, Compound B: (R,S)-2-(E)-(3,4-dichlorophenylmethylene)-1-(E)-[(3-dipropylamino-2-hydroxypropoxy)imino]cyclohexane, Compound C: (R,S)-2-(E)-(phenylmethylene)-1-(E)-[(3-hexylamino-2-hydroxypropoxy)imino]cyclohexane, Compound D: (R,S)-2-(E)-(4-chlorophenylmethylene)-1-(E)-[3'-(N-methyl-N-cyclohexylamino)-2'-hydroxypropoxyimino]cyclohexane, Compound E: (R,S)-2-(E)-(4-chlorophenylmethylene)-1-(E)-[(3-cyclohexylamino-2-hydroxypropoxy)imino]cyclohexane, Compound F: (R,S)-2-(E)-(4-chlorophenylmethylene)-1-(E)-[(3-hexylamino-2-hydroxypropoxy)imino]-cyclohexane, Compound G: (R,S)-2-(E)-(4-chlorophenylmethylene)-1-(E)-[(3-dimethylamino-2-hydroxypropoxy)imino]cyclohexane, Compound H: (R,S)-2-(E)-(2-methoxyphenylmethylene)-1-(E)-{3-[4-(2-methoxyphenyl)-1-piperazinyl]-2-hydroxypropoxyimino}cyclohexane, Compound I: (R,S)-2-(E)-(4-chlorophenylmethylene)-1-(E)-[(3-propenylamino-2-hydroxypropoxy)imino]cyclohexane, Compound J: (R,S)-2-(E)-(4-chlorophenylmethylene)-1-(E)-[(3-diisopropylamino-2-hydroxypropoxy)imino]cyclohexane, Compound K; (R,S)-2-(E)-(4-bromophenylmethylene)-1-(E)-{[(3-(1'-methylethylamino)-2-hydroxypropoxy]imino}cyclohexane, Compound L: (R,S)-2-(E)-(4-chlorophenylmethylene)-1-(E)-[(3-butylamino-2-hydroxypropoxy)imino]cyclohexane and Compound M: (R,S)-2-(E)-(phenylmethylene)-1-(E)-{[3-(3-dimethylamino-1-propylamino)-2-hydroxypropoxy]imino}cyclohexane.

The cyclic ketone derivatives of the formula I can be prepared by using the process described in the GB Patent No. 2,235,198. Essentially, the known process comprises
a) reacting a ketone of the formula II

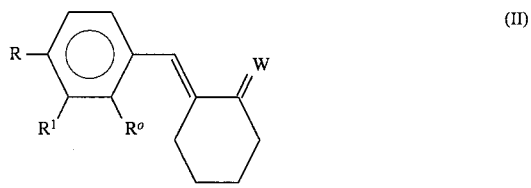

(II)

wherein W represents oxygen, R and $R^1$ independently stand for hydrogen or halo, and $R^0$ means hydrogen or a $C_{1-4}$ alkoxy group, with a hydroxylamine derivative of the formula III

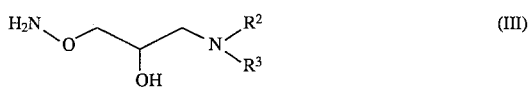

(III)

wherein $R^2$ and $R^3$ are as defined under formula I or an acid addition salt thereof; or b) reacting an oxime of the formula II, wherein W stands for a group of the formula =N—OH, R, $R^1$ and $R^0$ are as defined above, with an 1-halo-2,3-epoxypropane, then aminating the thus-obtained epoxypropyl derivative of the formula IV

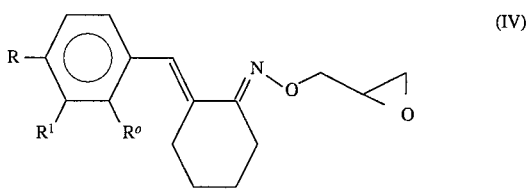

(IV)

wherein R, $R^1$ and $R^0$ are as defined above, with an organic base of the formula V

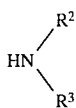

wherein $R^2$ and $R^3$ are as defined above, and, if desired, converting a cyclic ketone derivative of the formula I to a pharmaceutically acceptable acid addition salt or quaternary ammonium salt or, if desired, liberating the free base from a salt thereof and/or separating the stereoisomers and/or the optically active isomers.

The salts of the compounds of the formula I formed with pharmaceutically acceptable acids may be the salts of inorganic or organic acids commonly used in the pharmaceutical industry (e.g. salts of inorganic acids such as sulfuric acid, hydrogen chloride,. hydrogen bromide, phosphoric acid; or salts of organic acids such as acetic, propionic, methanesulfonic, p-toluenesulfonic, tartaric, succinic, maleic, fumaric, citric, malic or lactic acid and the like).

The activity of the cyclic ketone derivatives of the formula I suitable to be used as active ingredients of the pharmaceutical compositions of the invention was proved by the following tests.

1. Acute toxicity

The acute toxicity was determined on NMRI strain mice of both sexes weighing 20 to 25 g each by using 6 animals for each dose. The compounds to be tested were administered perorally in a volume of 20 ml/kg, the highest dose applied was 1000 mg/kg. After the administration the animals were kept under usual laboratory conditions for 7 days. The $LD_{50}$ values were calculated according to the method of Litchfield and Wilcoxon /J. Pharmacol. Exp. Ther., 96, 99 (1949)/. The results obtained are shown in Table I.

TABLE I

| Compound tested | $LD_{50}$ p.o. in mg/kg |
|---|---|
| A | higher than 1000 |
| B | higher than 1000 |
| C | higher than 1000 |
| D | higher than 1000 |
| E | higher than 1000 |
| F | higher than 1000 |
| G | higher than 1000 |
| H | higher than 1000 |
| I | about 1000 |
| J | 1000 |
| K | about 1000 |
| L | 1300 |
| M | higher than 1000 |
| omeprazole | higher than 4000 |
| cimetidine | 2600 |
| cetraxate | higher than 1000 |

The data given as "higher than" a certain value mean the highest dose administered without noting any death of animals.

2. Comparison of the gastroprotective and gastric acid secretion inhibiting effects 2.1. Test with absolute ethanol Rats of both sexes weighing 200 to 250 g, each previously starved for 24 hours, were used in this experiment. The lesions of gastric mucosa were induced by the oral administration of absolute ethanol in a dose of 1 ml/animal. After one hour following the administration, the animals were killed by an overdose of ether, the stomach was excised and the alterations of gastric mucosa were examined. The lengths of the erosions were measured and summarized (expressed in mm) for each stomach to obtain the erosion index by calculating the average value of the group. The inhibition was calculated in percentage by comparing the value of the group treated with ethanol to that of the control group treated only with the vehicle. Various doses of the compounds to be tested were administered, perorally, in a volume of 5 ml/kg using a pretreatment time of 60 minutes. Eight rats were used for each dose. /A. Robert, Gastroenterology 77, 761–767 (1979)/.

2.2. Effect on the gastric acid secretion

The influence of the compounds on the gastric acid secretion was examined on starved Wistar rats of both sexes weighing 180 to 240 g each by using Shay's method /H. Shay et al., Gastroenterology, 5, 45 (1945)/. The compounds to be tested were given, perorally, 3 hours before the ligation of the pylorus. Four hours after the operation, the animals were killed by an overdose of ether, the stomach was excised, the stomach content was centrifuged and the free hydrochloric acid content of the gastric juice was determined by titration in the presence of Töpfer's reagent. The percentage of inhibition and then the $ED_{50}$ values were determined by calculating average values for the groups and comparing those to the average values for the control group.

The data obtained are summarized in Table II.

TABLE II

| | Gastroprotective activity | |
|---|---|---|
| Compound tested | Test with absolute ethanol, $ED_{50}$ p.o. in mg/kg | Relative activity related to the inhbition of the free acid* |
| A | 2.0 | 60.5 |
| B | 12.6 | 12.5 |
| C | 0.8 | about 250.0 |
| D | 2.6 | 32.3 |
| E | 6.1 | 30.0 |
| F | 4.6 | 25.0 |
| G | 0.8 | 60–125 |
| H | 9.5 | higher than 20.0 |
| I | 8.4 | higher than 10.0 |
| J | 7.0 | about 25.0 |
| K | 6.7 | about 17.9 |
| L | 7.6 | 18.3 |
| M | 29.9 | about 6.7 |
| omeprazole | 4.5 | 0.9 |
| cimetidine | 100–200 | 0.3–0.6 |
| pirenzepine** | 18.6 | 0.4 |
| sucralfate | 69.0 | — |
| cetraxate | 76.4 | higher than 4 |

*Relative activity = $ED_{50}$ value of the gastric acid inhibition related to the $ED_{50}$ value of the inhibition of the gastric erosion.
**5,11-Dihydro-11-[(4-methyl-1-piperazinyl)acetyl]-6H-pyrido-/2,3-b//1,4/benzodiazepin-6-one.

In the test with absolute ethanol which is useful for showing the gastroprotective activity, as to the effective dose range, a sharp difference can be made between the cytoprotective effect and the gastric acid inhibition, the latter resulting in the inhibition of the gastric erosion.

From Table II it can be seen that the three reference compounds used in the therapy of ulcer and having a mechanism of free acid inhibition, i.e. omeprazole, cimetidine and pirenzepine, exert a low gastroprotective action in a rather high dose; their relative activity amounts to only 0.3 to 0.9. This fact indicates that the above free acid inhibiting reference compounds protect the gastric mucosa against absolute ethanol as a consequence of their gastric acid inhibiting action.

As to the cyclic ketone derivatives tested, their relative activity is very high compared to that of the reference compounds, a fact proving that the cytoprotective effect of the cyclic ketone derivatives of the formula I, which appears in the protection of the gastric mucosa, is independent of the acid inhibition activity.

Both reference compounds having gastroprotective effect, i.e. sucralfate and cetraxate, exert nearly identical activity in the test with absolute ethanol, whereas the compounds of the formula I are effective in doses lower by one or two order(s).

2.3. Test with ethanol containing hydrochloric acid

The principle of the method consists in that, simultaneously with the administration of absolute ethanol, hydrochloric acid is introduced to the stomach. Thus, the influence on systemic gastric acid inhibition action can be eliminated by the presence of the exogenous acid.

The reagent used in this test was a mixture of concentrated aqueous hydrochloric acid and absolute ethanol in a mass ratio of 1 to 50 in accordance with the dilution ratio used by Yamazaki et al., see Japan J. Pharmacol., 55, 415–424 (1991). Otherwise, the experiment was performed as described under test 2.1., however, in addition to the erosion index calculated from the lengths of the erosions in mm, the ratio of occurence of animals showing at least one gastric erosion within a test group, i.e. the erosion frequency, was also evaluated. The results obtained are shown in Table III.

In Table III, in case of the inhibition of the erosion frequency, the activity of the compounds tested were related to that of cetraxate to obtain the relative activity.

In case of the inhibition of the erosion index, the $ED_{50}$ value Of cetraxate was divided by the $ED_{50}$ value of the compound tested to obtain the relative activity.

TABLE III

| Compound tested | Inhibition of the erosion frequency | | Inhibition of the erosion index | |
| --- | --- | --- | --- | --- |
| | $ED_{50}$ p.o. in mg/kg | Relative activity | $ED_{50}$ p.o. in mg/kg | Relative activity |
| A | 18.8 | 10.1 | 7.1 | 3.1 |
| B | 20.1 | 6.4 | 12.7 | 1.7 |
| C | 25.7 | 7.4 | 11.5 | 1.9 |
| D | 8.3 | 22.8 | 5.2 | 4.2 |
| E | 30–60 | 3–6 | 10.3 | 2.1 |
| F | 25.2 | 7.5 | 7.2 | 3.1 |
| G | 30–60 | 3–6 | 15.8 | 1.4 |
| H | h.t. 60 | l.t. 3 | 30–60 | 0.4–0.7 |
| I | 39.2 | 4.8 | 8.6 | 2.6 |
| J | 19.1 | 9.9 | 5.9 | 3.7 |
| K | 15–30 | 6–12 | 11.4 | 1.9 |
| L | 30–60 | 3–6 | 9.8 | 2.2 |
| M | 30–60 | 3–6 | 17.5 | 1.3 |
| cetraxate | 189.0 | 1.0 | 22.0 | 1.0 | h.t. = higher than
l.t. = lower than

From Table III it follows that the direct cytoprotective activity of the compounds of the formula I is substantially higher than that of the cetraxate used as reference compound, although the number of lesions in the gastric mucosa was increased and the lesions became more severe due to the presence of hydrochloric acid in the ethanol.

In the test according to Shay (section 2.2.), only a moderate gastric acid secretion inhibition was shown by the compounds of the formula I as well as by cetraxate having cytoprotective activity. In the above test (section 2.3.), the high activity of the compounds of the formula I in the presence of exogenous hydrochloric acid precludes the possibility that the acid inhibition effect would be predominant in the gastroprotective activity of the compounds.

3. Antibacterial effect on *Helicobacter pylori*

Helicobacter pylori strains used in these experiments were obtained from the biopsial samples of the stomachs of patients suffering from ulcerative diseases of the gastrointestinal system. From the pure culture of isolates a thick suspension was prepared with cysteine-inositol solution suitable for lyophilisation, and the suspension obtained was maintained in cold-resistant plastic ampoules in a deep-freezing chamber at a temperature of about −196 ° C. For the determination of the inhibitory effect of the compounds tested on *Helicobacter pylori*, blood agar containing 10 mg/liter of vancomycin and 25 mg/liter of amphotericin B was used /C. A. M. McNulty and I. C. Dent: Susceptibility of clinical isolates of *Campylobacter pylori* to twenty one antimicrobial agents. Book of Abstracts, 4th European Congress of Clinical Microbiology, Nice (1989)/.

Vancomycin is a stereoisomer of 23-(aminocarbonyl)-12-[[2-O-(3-amino-2,3,6-trideoxy-3-C-methyl-alpha-L-lyxo-hexopyranosyl)-beta-D-glucopyranosyl]oxy]-8,16-dichloro-2,3,4,5,19,20,21,22,23,24,25,26,27,28,29,30-hexadecahydro-5,19,34,36,38-pentahydroxy-28-[[(4-methyl-2-(methylamino)-1-oxopentyl]amino]-3,21,25,28,41-pentaoxo-1H-6,9:15,18-dietheno-4,30-(iminomethano)-31,35-metheno-11,27,13-/1/-propene/ 1,2/diyl/3/ylidene-13H-10,14,2,22,26,29-benzodioxatetraazacycloheptatriacontine-1-carboxylic acid.

Amphotericin B is [1R-(1R$^x$,3S$^x$,5R$^x$,6R$^x$,9R$^x$,11R$^x$,15S$^x$, 16R$^x$,17R$^x$,18S$^x$,19E,21E,23E,25E,27E,29E,31E,33R$^x$, 35S$^x$,36R$^x$,37S$^x$)]-33-[(3-amino-3,6-dideoxy-beta-D-mannopyranosyl)-oxy]-1,3,5,6,9,11,17,37-octahydroxy-15,16, 18-trimethyl-13-oxo-14,39-dioxabicyclo-/33.3.1/ nonatriaconta-19,21,23,25,27,29,31-heptaene-36-carboxylic acid.

The plates containing the strains were cultivated at 37° C. for 72 hours under a gaseous atmosphere containing 10 per cent of carbon dioxide and 5 per cent of oxygen /D. M. Jones et al., J. Clin. Pathol., 37, 1002 (1984)/.

The culture media were inoculated by diluting the broth culture of the strains grown overnight or with a suspension prepared from a culture obtained on a solid medium. About $10^5$ of germs were applied to the surface of each plate.

A series of dilution were prepared from the compound to be-tested. The MIC (minimal inhibiting concentration) value of the compounds tested was considered to be the lowest concentration inhibiting the growth of the test organism completely. The results obtained for compounds C, D, F and G as well as cetraxate used as reference are given in Table IV.

TABLE IV

| *Helicobacter* pylori strains | Compounds | | | | MIC value in microgram/ml of cetraxate |
| --- | --- | --- | --- | --- | --- |
| | C | D | F | G | |
| 867/90 | 3.9 | 15.6 | 1.9 | 31.2 | h.t. 500 |
| 1596 | 7.8 | 15.6 | 0.9 | 125 | h.t. 500 |
| 3842 | 3.9 | 15.6 | 1.9 | 62.5 | h.t. 500 |
| 6656 | 3.9 | 15.6 | 1.9 | 31.2 | h.t. 500 |
| 6709 | 3.9 | 15.6 | 1.9 | 125 | h.t. 500 |

$^x$h.t. = higher than

From Table IV it can be seen that the compounds of the formula I are extremely effective, thus, they can be used in the therapy of *Helicobacter pylori* infections. The MIC value of cetraxate must be much higher than 500 since in the tests cetraxate was found to be ineffective at the concentration indicated.

Thus, the cyclic ketone derivatives of the formula I possess excellent cytoprotective and antimicrobial effects, consequently, they can be advantageously used for the treatment of gastrointestinal diseases, where the gastrointestinal mucosa is injured or the weakening of the protective factors plays a pathogenic role, e.g.:

long-lasting treatment of rheumatoid diseases with non-steroidal antiinflammatory drugs;

ulcers, especially duodenal ulcers, that cannot be treated with antiulcer drugs that inhibit gastric acid;

chronic erosive gastritis (wherein the acid secretion is within the normal limits);

bacterial infections caused, in the first place, by *Helicobacter pylori* playing a significant role in the relapse of gastroduodenal diseases.

The known weak gastric acid secretion inhibiting activity of the compounds of the formula I does not play any essential role in their valuable novel gastroprotective effect.

On the basis of their valuable effects outlined above, the cyclic ketone derivatives of the formula I or their stereoisomers or optical isomers or possible mixtures thereof or pharmaceutically acceptable acid addition salts or quaternary ammonium salts thereof can be used as the active ingredients of pharmaceutical compositions having gastroprotective activity combined with antimicrobial effect against *Helicobacter pylori.*

The pharmaceutical compositions of the invention can be prepared by admixing the active ingredient to one or more pharmaceutically acceptable carrier(s), and converting the mixture obtained to a pharmaceutical composition by the known methods of the drug manufacture. As to the additives and methods see e.g. Remington's Pharmaceutical Sciences, 18th Edition, Mack Publishing Company, Easton, USA.

In general, the pharmaceutical compositions of the invention are suitable for peroral, rectal or parenteral administration or for local treatment.

For oral administration, powders, tablets, coated tablets, dragées, capsules etc. may be prepared. These dosage units contain, in general, 10 to 100 mg of active ingredient in addition to one or more carrier(s) that may be binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethylene glycol), silica etc.

The liquid pharmaceutical compositions used for oral administration are preferably aqueous suspensions and/or elixirs and can be prepared by using solvents or diluents such as water, ethanol, propylene glycol, glycerol etc.; suspending agents such as gelatine, carboxymethylcellulose etc.; taste improving agents such as sorbitol, sugar solution etc.; preservatives such as methyl p-hydroxybenzoate; as well as dyes.

Pharmaceutical compositions suitable for parenteral administration consist of sterile solutions of the active ingredient.

The pharmaceutical composition of the invention contains, in general, 0.1 to 95.0 per cent of the active substance. A typical dose for adult patients amounts to 0.25 to 40 mg/kg, preferably 1 to 20 mg/kg of the compound of the formula I or a pharmaceutically acceptable acid addition salt or quaternary ammonium derivative thereof, in a single daily dose or in 2 to 3 subdoses. In each case, the dose to be administered depends on the activity of the active ingredient used, route of administration, condition of the patient to be treated and other factors.

The invention also refers to a method for the treatment of gastrointestinal diseases connected with infections caused by *Helicobacter pylori* which comprises administering an effective non-toxic dose of a compound of the formula I or its stereoisomer or optical isomer or a possible mixture thereof, or a pharmaceutically acceptable acid addition salt or quaternary ammonium salt thereof to a patient suffering from gastrointestinal disorders.

The invention is illustrated in detail by the following non-limiting Examples.

EXAMPLE 1

Preparation of Tablets

| Composition | Amount in mg/tablet |
|---|---|
| Active ingredient of the formula I | 25.0 |
| Corn starch | 97.0 |
| Poly(vinylpyrrolidone) | 175.0 |
| Magnesium stearate | 3.0 |
| | 300.0 |

The active ingredient and corn starch are wetted with a 15 per cent aqueous poly(vinylpyrrolidone) solution, then granulated, and the wet granules are dried at 40° to 45 ° C. The dried granules are thoroughly mixed with magnesium stearate, and the mixture is compressed to obtain tablets weighing 300.0 mg each.

EXAMPLE 2

Preparation of Dragées

| Composition | Amount in mg/dragée |
|---|---|
| Active ingredient of the formula I | 50.0 |
| Lactose | 94.0 |
| Magnesium stearate | 2.0 |
| Poly(vinylpyrrolidone) | 4.0 |
| | 150.0 |

EXAMPLE 3

Preparation of Capsules

| Composition | Amount in mg/capsule |
|---|---|
| Active ingredient of the formula I | 25.0 |
| Corn starch | 122.0 |
| Colloidal silica | 3.0 |
| | 150.0 |

The ingredients listed are homogenized and the mixture obtained is filled into hard gelatine capsules. Each capsule contains 150 mg of the powder mixture.

We claim:

1. A method for the treatment of gastrointestinal diseases connected with infections caused by *Helicobacter pylori*, which comprises administering an effective non-toxic dose of a compound of the formula I

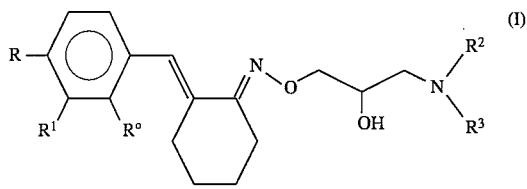

wherein

R and R¹ mean independently hydrogen or halo;

R⁰ stands for hydrogen or a $C_{1-4}$ alkoxy group;

R² and R³ independently represent hydrogen, a straight or branched chain $C_{1-8}$ alkyl optionally substituted by a dimethylamino group, a $C_{2-6}$ alkenyl or a $C_{3-7}$ cycloalkyl group; or $R^2$ and $R^3$ together with the adjacent nitrogen atom form a 6-membered heterocyclic group containing an additional nitrogen atom that may bear a phenyl group optionally substituted by a $C_{1-4}$ alkoxy group;

or a stereoisomer or optical isomer or a possible mixture thereof, or a pharmaceutically acceptable acid additional salt or quaternary ammonium salt thereof to a patient suffering from gastrointestinal disorders.

* * * * *